(12) United States Patent
Altug et al.

(10) Patent No.: US 10,436,711 B2
(45) Date of Patent: Oct. 8, 2019

(54) PLASMONIC NANOHOLE ARRAYS ON HYBRID SUBSTRATE FOR HIGHLY SENSITIVE LABEL-FREE BIOSENSING

(71) Applicant: ECOLE POLYTECHNIQUE FEDERALE DE LAUSANNE (EPFL), Lausanne (CH)

(72) Inventors: Hatice Yanik Altug, Mex (CH); Arif Engin Cetin, Lausanne (CH)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 273 days.

(21) Appl. No.: 15/214,568

(22) Filed: Jul. 20, 2016

(65) Prior Publication Data
US 2017/0023476 A1   Jan. 26, 2017

Related U.S. Application Data

(60) Provisional application No. 62/194,866, filed on Jul. 21, 2015.

(51) Int. Cl.
*G01N 21/59* (2006.01)
*H01J 37/317* (2006.01)
*G03F 7/20* (2006.01)
*G03F 7/42* (2006.01)

(52) U.S. Cl.
CPC ........... *G01N 21/59* (2013.01); *G03F 7/2037* (2013.01); *G03F 7/427* (2013.01); *H01J 37/3174* (2013.01); *G01N 2021/5903* (2013.01)

(58) Field of Classification Search
CPC ............ G01N 2021/5903; G01N 21/59; G03F 7/2037; G03F 7/427; H01J 37/3174; Y10T 436/24; Y10T 436/2575
USPC ..... 436/164, 165, 171, 173, 180; 422/82.05, 422/82.09
See application file for complete search history.

(56) References Cited

U.S. PATENT DOCUMENTS

| | | | |
|---|---|---|---|
| 8,009,356 B1 * | 8/2011 | Shaner | G02B 27/56 359/288 |
| 2013/0065777 A1 * | 3/2013 | Altug | G01N 21/554 506/9 |

OTHER PUBLICATIONS

Cetin et al. ACS Photonics, vol. 2, Jul. 29, 2015, pp. 1167-1174.*
Turkmen et al. Proceedings of the SPIE, vol. 8976, 2014, pp. 8976E-1-8976E-7.*
A• imovi• , Srdjan S., et al. "LSPR chip for parallel, rapid, and sensitive detection of cancer markers in serum." Nano letters 14.5 (2014): 2636-2641.
Acimovic, Srdjan S., et al. "Plasmon near-field coupling in metal dimers as a step toward single-molecule sensing." ACS nano 3.5 (2009): 1231-1237.

(Continued)

*Primary Examiner* — Maureen Wallenhorst
(74) *Attorney, Agent, or Firm* — Andre Roland S.A.; Nikolaus Schibli

(57) ABSTRACT

A biosensor device including a metal layer, a transparent substrate layer, and a dielectric layer, wherein the metal layer includes a plurality of sub-wavelength apertures, and wherein the dielectric layer is located between the metal layer and the transparent substrate layer to form a spectrally isolated and well-defined optical transmission resonance through the extraordinary optical transmission (EOT) phenomenon.

15 Claims, 14 Drawing Sheets

(56) References Cited

OTHER PUBLICATIONS

Anker, Jeffrey N., et al. "Biosensing with plasmonic nanosensors." Nature materials 7.6 (2008): 442-453.
Artar, Alp, Ahmet Ali Yanik, and Hatice Altug. "Fabry-Pérot nanocavities in multilayered plasmonic crystals for enhanced biosensing." Applied Physics Letters 95.5 (2009): 051105.
Blanchard-Dionne, A. P., et al. "Intensity based surface plasmon resonance sensor using a nanohole rectangular array." Optics express 19.16 (2011): 15041-15046.
Bronner, V. T., M. Tabul, and T. Bravman. "Rapid Screening and Selection of Optimal Antibody Capturing Agents Using the ProteOn XPR36 Protein Interaction Array System." Bio-Rad Technical Note 5820 (2006).
Cetin, Arif E., and Hatice Altug. "Fano resonant ring/disk plasmonic nanocavities on conducting substrates for advanced biosensing." ACS nano 6.11 (2012): 9989-9995.
Cetin, Arif E., et al. "Handheld high-throughput plasmonic biosensor using computational on-chip imaging." Light: Science & Applications 3.1 (2014): e122.
Chang, Tsung-Yao, et al. "Large-scale plasmonic microarrays for label-free high-throughput screening." Lab on a Chip 11.21 (2011): 3596-3602.
Cinel, Neval A., Serkan Bütün, and Ekmel Özbay. "Electron beam lithography designed silver nano-disks used as label free nano-biosensors based on localized surface plasmon resonance." Optics express 20.3 (2012): 2587-2597.
Coskun, Ahmet F., et al. "Lensfree optofluidic plasmonic sensor for real-time and label-free monitoring of molecular binding events over a wide field-of-view." Scientific reports 4 (2014): 6789.
Dahlin, Andreas B., Jonas O. Tegenfeldt, and Fredrik Höök. "Improving the instrumental resolution of sensors based on localized surface plasmon resonance." Analytical chemistry 78.13 (2006): 4416-4423.
Dickson, Wayne, et al. "Electronically controlled surface plasmon dispersion and optical transmission through metallic hole arrays using liquid crystal." Nano letters 8.1 (2008): 281-286.
Donath, Edwin. "Biosensors: Viruses for ultrasensitive assays." Nature nanotechnology 4.4 (2009): 215-216.
Eftekhari, Fatemeh, et al. "Polarization-dependent sensing of a self-assembled monolayer using biaxial nanohole arrays." Applied Physics Letters 92.25 (2008): 253103.
Gao, Hanwei, Joel Henzie, and Ted W. Odom. "Direct evidence for surface plasmon-mediated enhanced light transmission through metallic nanohole arrays." Nano letters 6.9 (2006): 2104-2108.
Gao, Yongkang, et al. "Plasmonic interferometric sensor arrays for high-performance label-free biomolecular detection." Lab on a Chip 13.24 (2013): 4755-4764.
Gao, Yongkang, Qiaoqiang Gan, and Filbert J. Bartoli. "Spatially selective plasmonic sensing using metallic nanoslit arrays." IEEE Journal of Selected Topics in Quantum Electronics 20.3 (2014): 96-101.
Hendry, Euan, et al. "Ultrasensitive detection and characterization of biomolecules using superchiral fields." Nature nanotechnology 5.11 (2010): 783-787.
Huang, Min, et al. "Actively transporting virus like analytes with optofluidics for rapid and ultrasensitive biodetection." Lab on a Chip 13.24 (2013): 4841-4847.
Im, Hyungsoon, et al. "Nanohole-based surface plasmon resonance instruments with improved spectral resolution quantify a broad range of antibody-ligand binding kinetics." Analytical chemistry 84.4 (2012): 1941-1947.
Lee, Kuang-Li, and Pei-Kuen Wei. "Enhancing surface plasmon detection using ultrasmall nanoslits and a multispectral integration method." Small 6.17 (2010): 1900-1907.
Li, Jiaqi, et al. "Revisiting the surface sensitivity of nanoplasmonic biosensors." Acs Photonics 2.3 (2015): 425-431.
Liu, Na, et al. "Nanoantenna-enhanced gas sensing in a single tailored nanofocus." Nature materials 10.8 (2011): 631-636.
Mazzotta, Francesco, et al. "Influence of the evanescent field decay length on the sensitivity of plasmonic nanodisks and nanoholes." Acs Photonics 2.2 (2015): 256-262.
Otte, Marinus A., et al. "Improved biosensing capability with novel suspended nanodisks." The Journal of Physical Chemistry C 115.13 (2011): 5344-5351.
Päivänranta, Birgit, et al. "High aspect ratio plasmonic nanostructures for sensing applications." ACS nano 5.8 (2011): 6374-6382.
Piliarik, Marek, and Vahid Sandoghdar. "Direct optical sensing of single unlabelled proteins and super-resolution imaging of their binding sites." Nature communications 5 (2014).
Qiu, Liping, et al. "Cell membrane-anchored biosensors for real-time monitoring of the cellular microenvironment." Journal of the American Chemical Society 136.38 (2014): 13090-13093.
Ruemmele, Julia A., et al. "A localized surface plasmon resonance imaging instrument for multiplexed biosensing." Analytical chemistry 85.9 (2013): 4560-4566.
Schatz, George C., Jeffrey M. McMahon, and Stephen K. Gray. "Tailoring the parameters of nanohole arrays in gold films for sensing applications." NanoScience+ Engineering. International Society for Optics and Photonics, 2007.
Stewart, Matthew E., et al. "Quantitative multispectral biosensing and 1D imaging using quasi-3D plasmonic crystals." Proceedings of the National Academy of Sciences 103.46 (2006): 17143-17148.
Tan, Chunlei, Janne Simonen, and Tapio Niemi. "Hybrid waveguide-surface plasmon polariton modes in a guided-mode resonance grating." Optics Communications 285.21 (2012): 4381-4386.
Thio, Tineke, et al. "Surface-plasmon-enhanced transmission through hole arrays in Cr films." JOSA B 16.10 (1999): 1743-1748.
Usoskin, A. I., and O. A. Popova. "Silicon nitride films: Optical properties and possibility of applications in multilayer interference systems." Journal of Applied Spectroscopy 43.5 (1985): 1268-1271.
Yanik, A. A.; Kamohara, O.; Artar, A.; Geisbert, T. W.; Connor J. H.; Altug, H. An optofluidic nanoplasmonic biosensor for direct detection of live viruses from biological media. Nano Lett., Oct. 2010, 4962-4969.
Yanik, Ahmet A., et al. "Seeing protein monolayers with naked eye through plasmonic Fano resonances." Proceedings of the National Academy of Sciences 108.29 (2011): 11784-11789.
Yanik, Ahmet Ali, et al. "Integrated nanoplasmonic-nanofluidic biosensors with targeted delivery of analytes." Applied physics letters 96.2 (2010): 021101.
Zeng, Beibei, Yongkang Gao, and Filbert J. Bartoli. "Differentiating surface and bulk interactions in nanoplasmonic interferometric sensor arrays." Nanoscale 7.1 (2015): 166-170.
Zhang, Wei, et al. "High sensitivity photonic crystal biosensor incorporating nanorod structures for enhanced surface area." Sensors and Actuators B: Chemical 131.1 (2008): 279-284.

* cited by examiner

PLASMONIC NANOHOLE ARRAYS ON HYBRID SUBSTRATE FOR HIGHLY SENSITIVE LABEL-FREE BIOSENSING

CROSS-REFERENCE TO RELATED APPLICATIONS

The present application claims priority to the U.S. provisional application 62/194,866, filed on Jul. 21, 2015, the entire contents thereof being herewith incorporated by reference.

FIELD OF THE INVENTION

The present invention is directed to the field of biosensors, more particularly biosensors made of nanohole arrays for multiplexed optical measurements, methods of operating such biosensors, and methods of manufacturing the nanohole arrays.

DISCUSSION OF THE BACKGROUND

Biosensors are essential in preventing epidemics for public and global health, warning of intentionally released agents for national security and defense, and fundamental biology and pharmacology research for early disease detection and drug discovery. These applications require biosensors that possess several critical properties for reliable and rapid detection. For instance, label-free biosensors can eliminate problems associated with labelling steps. Biosensors with ultra-sensitive optical responses can accurately distinguish minute changes in molecular level. Ability to operate in real-time can enable analysis of biomolecular binding kinetics. Massively multiplexed biosensors can allow parallel screening of large variety of biological assays. Portable biosensors that are easy-to-operate in a cost effective manner can be used in resource-poor settings. Recently, plasmonic biosensors utilizing nanoparticle and nanoaperture geometries have received significant attention as they can meet these needs.

In particular, nanohole arrays fabricated on optically thick metal films are highly promising. These subwavelength apertures enable extraordinary optical transmission (EOT) phenomenon due to the effective excitation of plasmons at normal incidence by grating coupling. This feature allows compact biosensors by eliminating the bulky prism-coupling mechanism needed by conventional surface plasmon resonance (SPR) sensors. Even though SPR schemes have very sensitive response of around 10-7 RIU (refractive index unit), their angle-sensitive optical setup limits large-area multiplexing and high-throughput biodetection. Plasmonic modes supported by nanohole arrays are highly sensitive to surface conditions due to their strong field enhancements and light confinement in nanometer scale. Consequently, local refractive index changes induced by the binding of minute quantities of biomolecules on the sensor surface can be detected by monitoring the spectral variations within the plasmonic modes without any need for fluorescent labels.

Nanohole arrays are also compatible with imaging-based devices and can be implemented in a microarray format for multiplexed and high-throughput biosensing. The optical extinction settings on collection of nanohole transmission could be implemented in optical settings that are cost-effective and portable. Recently, plasmonic nanoholes have been utilized in a lens free microscope with a normally incident light-emitting-diode (LED) source and a complementary metal-oxide semiconductor (CMOS) camera to demonstrate a low-cost handheld biosensor for resource-poor and field settings. Integrating with microfluidic systems, nanohole biosensors also enable real-time analysis of biomolecular binding kinetics.

As discussed above, plasmonic nanohole arrays have received significant attention as they have highly advantageous optical properties for ultra-sensitive and label-free biosensing applications. However, these subwavelength periodic apertures are mainly implemented on transparent materials, which results in multiple spectrally close transmission resonances. However, this spectral characteristic is not ideal for biosensing applications as it complicates monitoring spectral variations. In light of these and other deficiencies in the field of biosensing and the use of nanohole arrays, new and superior solutions are desired.

SUMMARY

According to one aspect of the present invention, a biosensor device is provided. The biosensor device preferably includes a metal layer, a transparent substrate layer, and a dielectric layer. Preferably, the metal layer includes a plurality of sub-wavelength apertures, and the dielectric layer is located between the metal layer and the transparent substrate layer to form a spectrally isolated and well-defined optical transmission resonance through the extraordinary optical transmission (EOT) phenomenon.

According to another aspect of the present invention, a method for carrying out bio-sensing is provided. Preferably, the method includes the steps of providing the biosensor device, the biosensor device including a metal layer, a transparent substrate layer, and a dielectric layer, the metal layer having a plurality of sub-wavelength apertures, and the dielectric layer located between the metal layer and the transparent substrate layer to form a spectrally isolated and well-defined optical transmission resonance through the extraordinary optical transmission (EOT) phenomenon, and providing at least one substance to be identified on the plurality of sub-wavelength apertures of the metal layer. Moreover, the method preferably includes a step of measuring an optical transmission spectrum of the at least one substance to be identified.

According to yet another aspect of the present invention, a method for manufacturing a biosensor is provided. The method preferably includes the steps of depositing gold layer onto a hybrid substrate made of a silicon nitride interlayer film and a fused silica substrate, performing lithography to define nanohole arrays in the gold layer and the silicon nitride interlayer film of the hybrid substrate, and etching the dielectric layer and the gold layer by ion beam using a resist as a mask. Moreover, the method preferably further includes the step of performing a plasma cleaning to remove remaining portions of the resist.

The above and other objects, features and advantages of the present invention and the manner of realizing them will become more apparent, and the invention itself will best be understood from a study of the following description with reference to the attached drawings showing some preferred embodiments of the invention.

BRIEF DESCRIPTION OF THE SEVERAL VIEWS OF THE DRAWINGS

The accompanying drawings, which are incorporated herein and constitute part of this specification, illustrate the presently preferred embodiments of the invention, and together with the general description given above and the detailed description given below, serve to explain features of the invention.

FIG. 2B shows arrows highlighting the suppression of Au/Glass modes with increasing silicon nitride thickness. Magnetic ($|H|^2$) and electric ($|E|^2$) field intensity distributions calculated at the corresponding transmission resonances for the aperture system on a glass substrate (FIG. 2C) and hybrid substrate (FIG. 2D) for 70 nm thick silicon nitride interlayer;

In FIG. 5A-5D, zoomed images are used to show the limit-of-detection (LOD) of the aperture systems;

Figure 8:
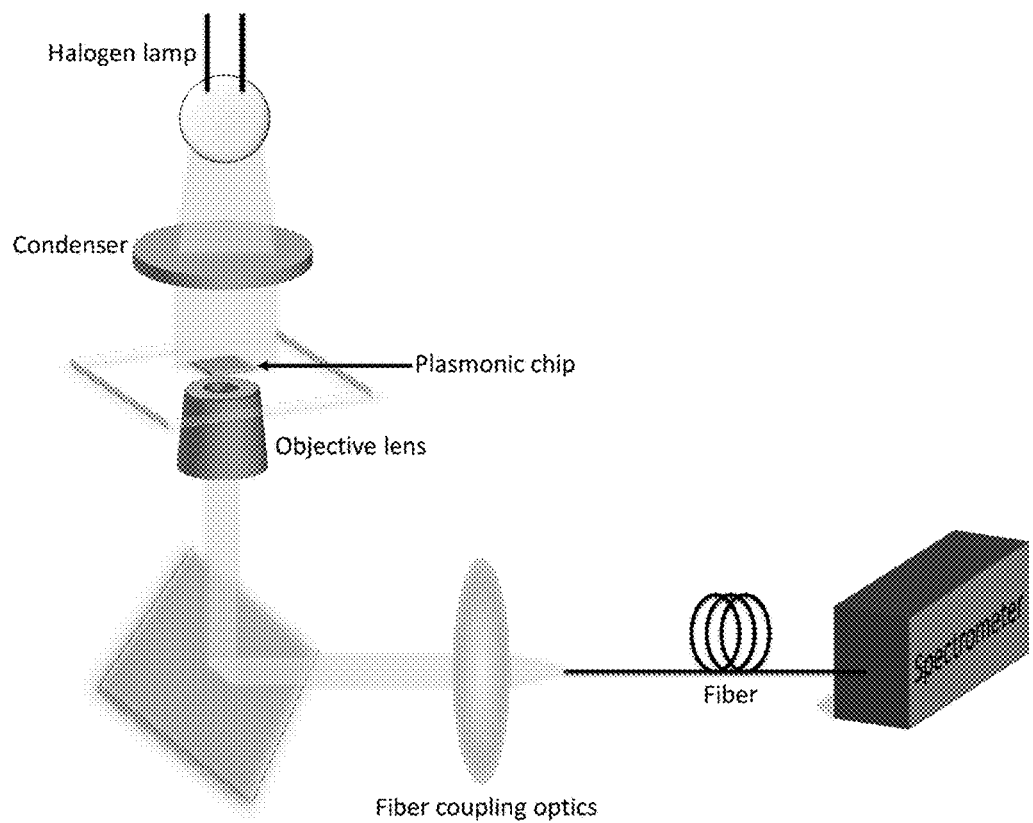
FIG. 8 shows a schematic representation of a system for the optical characterization of the nanohole arrays, according to another aspect of the present invention.
Figure 10:
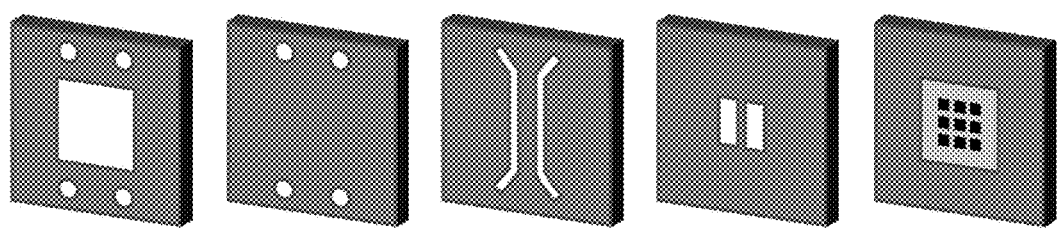
FIG. 10 show schematic representations of the layers of an exemplary different dual-channel microfluidic chamber, according to still another aspect of the present invention.

The images showing the nanohole arrays in FIG. 1A-1D, 2A-2D, FIG. 3A 4A-4B, and the representations in FIGS. 8 and 10 are simplified for illustration purposes and may not be depicted to scale.

DETAILED DESCRIPTION OF THE SEVERAL EMBODIMENTS

In accordance with one aspect of the present invention, a hybrid substrate is proposed for the nanohole array, including of a high refractive index dielectric interlayer over a transparent material. The dielectric layer has a refractive index higher than the transparent substrate, for example, SiN used as a dielectric with a refractive index of >2 versus glass as a substrate with a refractive index of 1.4, and it has been shown that gold nanohole arrays support spectrally isolated and well-defined plasmonic resonances that are easy-to-track. Compared to conventional configurations on transparent material, nanoholes on hybrid substrate also exhibit plasmonic modes with well-preserved amplitudes, which is useful for reliable spectral monitoring. Moreover, nanohole arrays on hybrid substrate are more sensitive to changes in surface conditions. Using a spectral integration method, which evaluates wavelength shifts in a large spectral window instead of monitoring only the plasmonic resonance wavelength, a detection limit as low as $2 \times 10^{-5}$ RIU is obtained. Furthermore, real-time monitoring of biomolecular binding interactions even at sub-1 ng/mL level has been demonstrated.

Figure 1A:
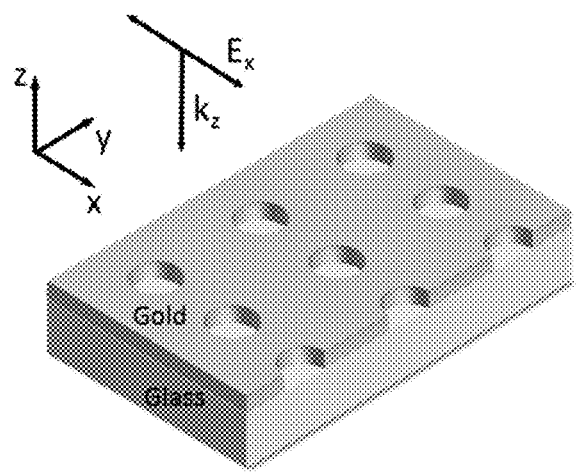
FIG. 1A depicts a schematic illustration of the gold nanohole arrays on glass made of fused silica with refractive index 1.42.
Figure 1B:
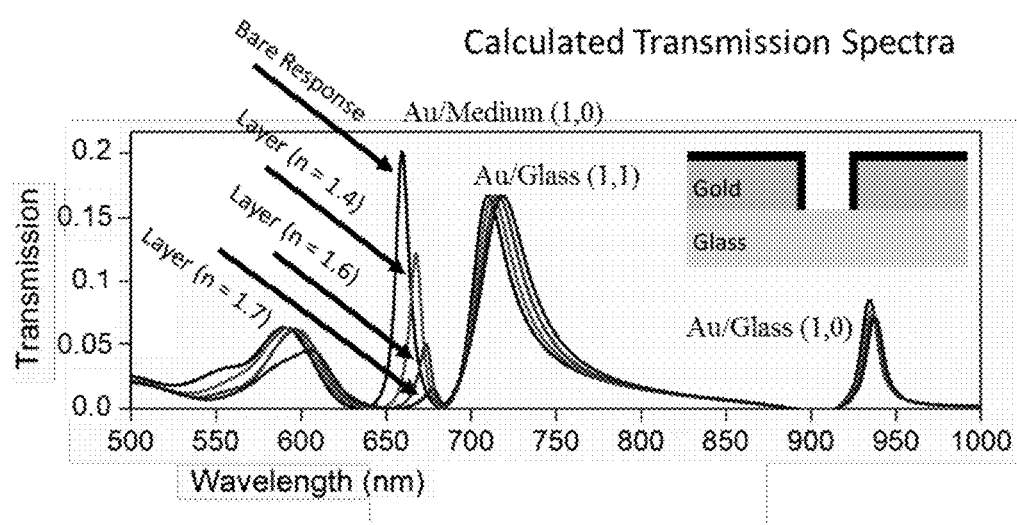
FIG. 1B shows the calculated transmission spectra for the gold nanohole arrays.

As shown in FIG. 1A, a nanohole array according to the background art is depicted. These nanohole designs are implemented directly on transparent materials, for example glass. FIG. 1B shows the EOT response of periodic nanohole arrays on glass covered with a thin layer of dielectric film of varying refractive indices, according to the background art. The EOT spectra have multiple resonance peaks that are spectrally close to each other. However, this is not well-suitable for biosensing applications requiring reliable and accurate identification of spectral shifts. For instance, due to the differences in the sensitivity of different plasmonic modes, their spectra start to merge which makes monitoring spectral variations difficult. Furthermore, the amplitude of the most sensitive mode Au/Medium(1,0), with an operation using air as the medium, significantly decreases as the refractive index of the coating layer increases.

Figure 1C:
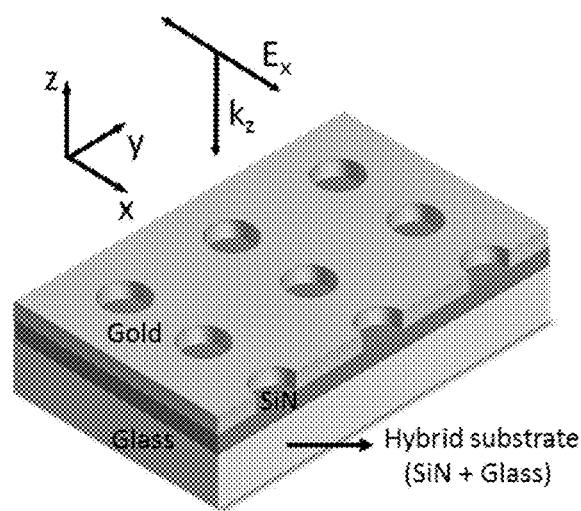
FIG. 1C depicts a schematic illustration of a hybrid substrate made of silicon nitride (SiN) and glass.
Figure 1D:
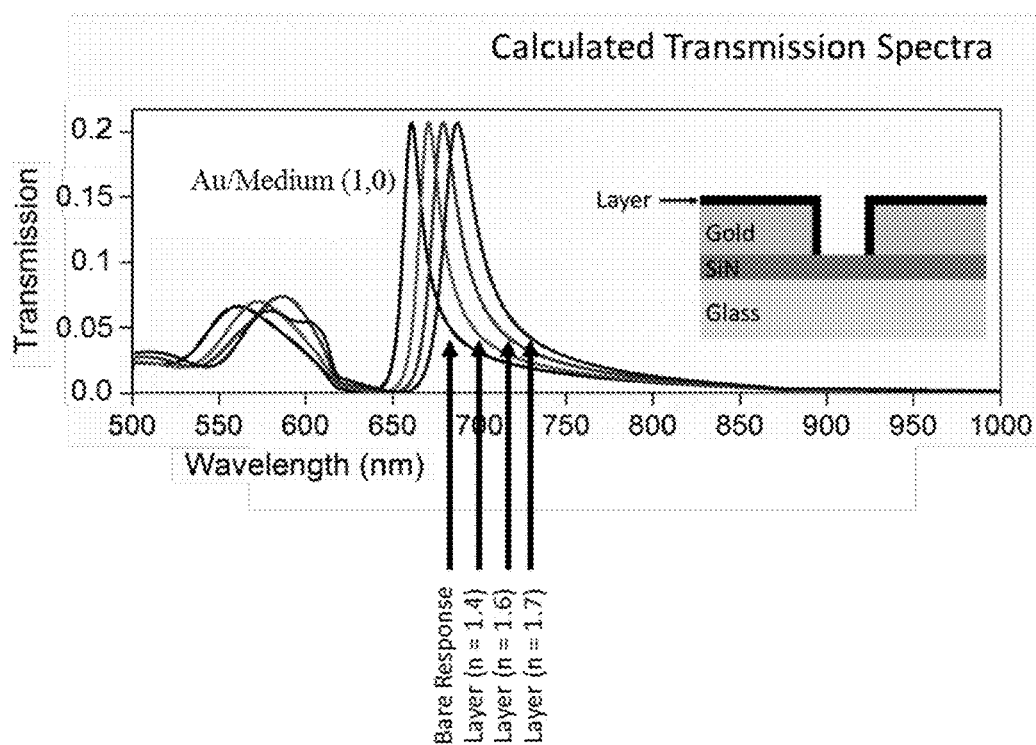
FIG. 1D shows the calculated transmission spectra of the nanohole arrays on the hybrid substrate, where the propagation and polarization directions of the illumination source used in the numerical calculations are shown.

In contrast, as shown in FIG. 1C, according to some aspects of the present invention, these problems to be overcome by inserting a high index dielectric material, e.g., a silicon nitride interlayer between the metallic film and the transparent supporting substrate. Using this hybrid substrate consisting of a silicon nitride (SiN) interlayer on glass, spectrally isolated and well-defined EOT signals which are easy-to-track are obtained. As further shown in FIG. 1D, compared to the conventional configuration on glass, according to one aspect of the present invention, in the nanoaperture system the amplitude of the transmission resonances is well-preserved. It has been shown that the nanoholes on the hybrid substrate support higher sensitivities. By utilizing a spectral integration method, in which the total shift in a spectral window instead of only the resonance peaks is monitored, substantial sensitivity improvements are obtained. Using the integration method according to an aspect of the present invention, a detection limit as low as $2\times10^{-5}$ RIU is observed, and real-time analysis of biomolecular binding interactions even below 1 ng/mL analyte concentration levels are shown.

In FIGS. 1B and 1D, the calculated transmission spectra of nanohole arrays with glass and hybrid substrate are shown, where the gold surface is covered with an 8 nm thick dielectric layer, illustrated with black in figure insets, with refractive indices: n=1.4, n=1.6 and n=1.7. The medium above the sensor coated with a thin dielectric layer is air. Aperture system on glass supports Au/Medium(1,0) [Medium=Air], Au/Glass(1,1) and Au/Glass(1,0) modes, while the one on hybrid substrate supports only Au/Medium (1,0) mode [Medium=Air]. The plasmonic mode of interest used in the sensing of the thin analyte layer is Au/Medium (1,0) [Medium=Air]. The preferred device parameters used in the simulations: Hole diameter is 200 nm, array periodicity is 600 nm, thicknesses of the gold film and silicon nitride interlayer are 120 nm and 70 nm, respectively.

Next, the nanohole arrays on glass and hybrid substrate are discussed. FIGS. 1A and 1B illustrate the exemplary gold nanohole designs utilizing glass and hybrid substrate, respectively. FIGS. 1B and 1D show their transmission spectra calculated for an x-polarized light source (black curve denotes the bare response). Numerical analyses are performed with Finite Difference Time Domain (FDTD) calculations, by Lumerical Solutions™. Nanohole arrays support multiple EOT resonances at peak wavelengths ($\lambda_{res}$) obeying the grating coupling condition:

$$\lambda_{res} = \frac{P}{\sqrt{i^2+j^2}} \sqrt{\frac{\varepsilon_d \varepsilon_m}{\varepsilon_d + \varepsilon_m}} \quad (1)$$

where $\varepsilon_d$ and $\varepsilon_m$ are the permittivity of dielectric and metal, P is the periodicity of the square array, and (i, j) are the grating orders along x- and y-directions. For the given spectral range, the nanohole system on glass with 200 nm hole diameter, 600 nm array periodicity and 120 nm gold thickness, supports 3 distinct transmission resonances due to Au/Medium(1,0) mode [Medium=Air], Au/Glass(1,1) and Au/Glass(1,0) mode excitations spectrally peaked at ~660 nm, ~710 nm and ~934 nm, respectively.

On the other hand, the one on hybrid substrate, utilizing a 70 nm thick silicon nitride interlayer on top of glass, supports only Au/Medium(1,0) mode [Medium=Air] at ~660 nm, and Au/Glass modes are no longer observed. For the excitation of EOT peak used for biosensing, it is important to properly adjust the nanohole diameter and periodicity. As indicated in Equation (1) above, the period and the refractive index of the media above and below the metal layer control the operation wavelength. In comparison to the period size and thus operation wavelength, the hole diameter should not be very small, for example $\lambda/10$, otherwise the transmission efficiency, for example the EOT signal strength, will drop significantly. On the other hand, the diameter should not be very large (e.g. $\lambda/2$). For 600 nm period, a suitable hole diameter is for example between 100 and 220 nm. Likewise, it is important to choose a proper metal thickness. An optically thin metal film will result in strong background transmission while a thick metal will compromise the signal strength of EOT and introduce high optical loss. For the wavelength range employed in this work (such as >500 nm), a suitable metal thickness is for example between 80 and 150 nm.

In order to compare the sensitivity of the nanoaperture systems, we perform FDTD simulations with an 8 nm thick dielectric layer, denoted in the insets of FIGS. 1B and 1D, covering only the gold film. FIGS. 1B and 1D show the transmission spectra of the two nanohole configurations in the presence of the dielectric layer with the refractive indices: n=1.4 (green curve) and n=1.6 (red curve). The medium above the dielectric coated gold sensor is air, which is indicated below as Medium=Air. For the aperture system on glass with n=1.4 [n=1.6], Au/Medium(1,0), Au/Glass(1, 1) and Au/Glass(1,0) modes shift by ~8 nm [~14 nm], ~2 nm [~6 nm] and ~2 nm [~3 nm], respectively. Au/Medium(1,0) mode provides the largest sensitivity compared to the others due to its highly accessible large local electromagnetic fields, which will be discussed in the next section. As Au/Medium(1,0) mode [Medium=Air] shifts to longer wavelengths, we observe a dramatic reduction in the transmission intensity due to its increasing spectral overlap with Au/Glass(1,1) mode.

This overlap is due to the difference between the sensitivities of Au/Medium(1,0) mode [Medium=Air] and Au/Glass(1,1) modes, in which the latter one shifts smaller. Importantly, when the refractive index of the thin dielectric layer on the sensor surface is increased to n=1.7 (blue curve), the transmission intensity of Au/Medium(1,0) mode [Medium=Air] strongly diminishes since Au/Glass(1,1) mode has much larger transmission intensity compared to Au/Medium(1,0) mode [Medium=Air]. In contrast, nanoholes on hybrid substrate according to one aspect of the present invention support only Au/Medium(1,0) mode [Medium=Air] within the presented spectral window. The system also shows higher sensitivities, for example with Au/Medium(1,0) mode [Medium=Air] red-shifts by as large as ~11 nm and ~19 nm for the refractive indices of the dielectric layer n=1.4 and n=1.6, respectively. In the absence of any spectral merging between different transmission resonances, Au/Medium(1,0) mode [Medium=Air] shifts to longer wavelengths with negligible amplitude variations. These features make the nanohole system on hybrid substrate highly suitable for biosensing applications.

Figure 2A:
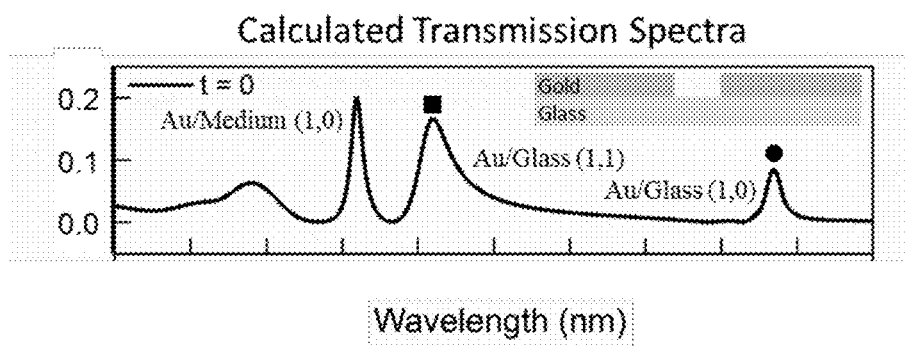
FIG. 2A shows calculated transmission spectra of the nanohole arrays on glass.
Figure 2B:
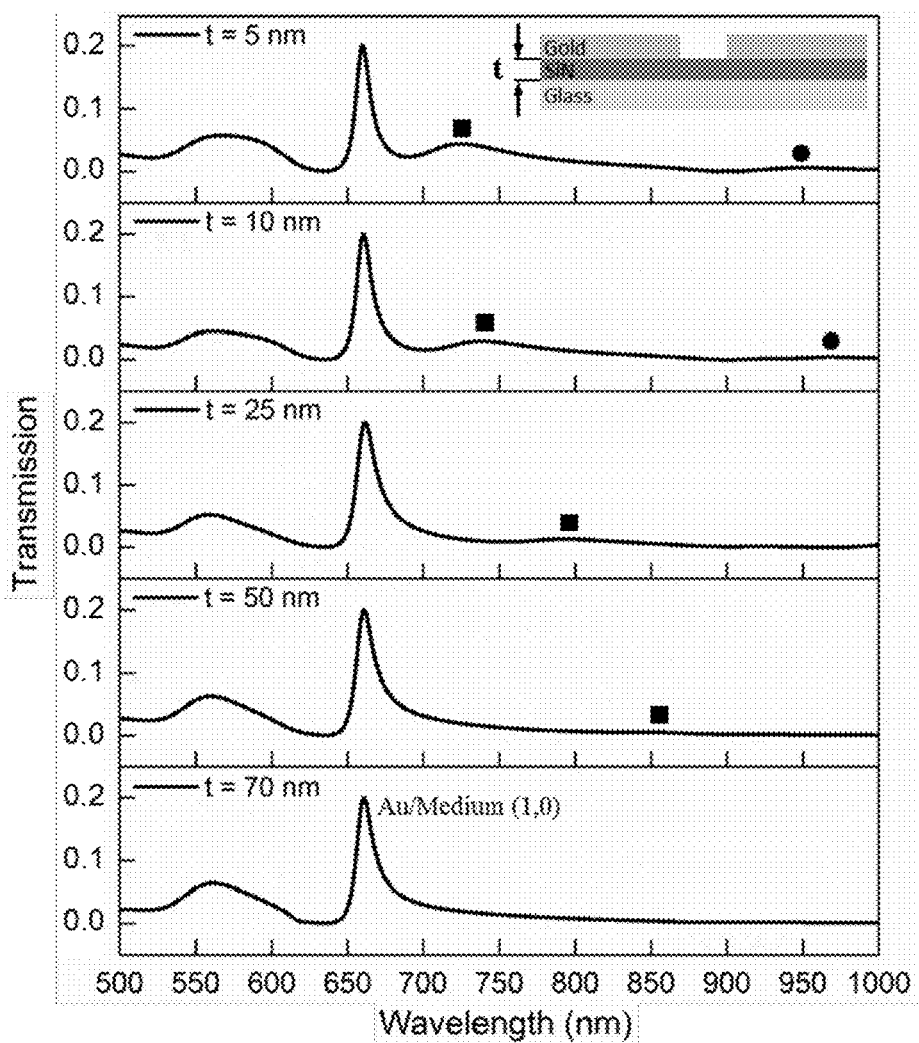
FIG. 2B shows calculated transmission spectra of the nanohole arrays on hybrid substrate, where the thickness t of the silicon nitride interlayer is varied from 5 nm to 70 nm, as schematically illustrated in the inset, where the medium above the structure is air.
Figure 2C:
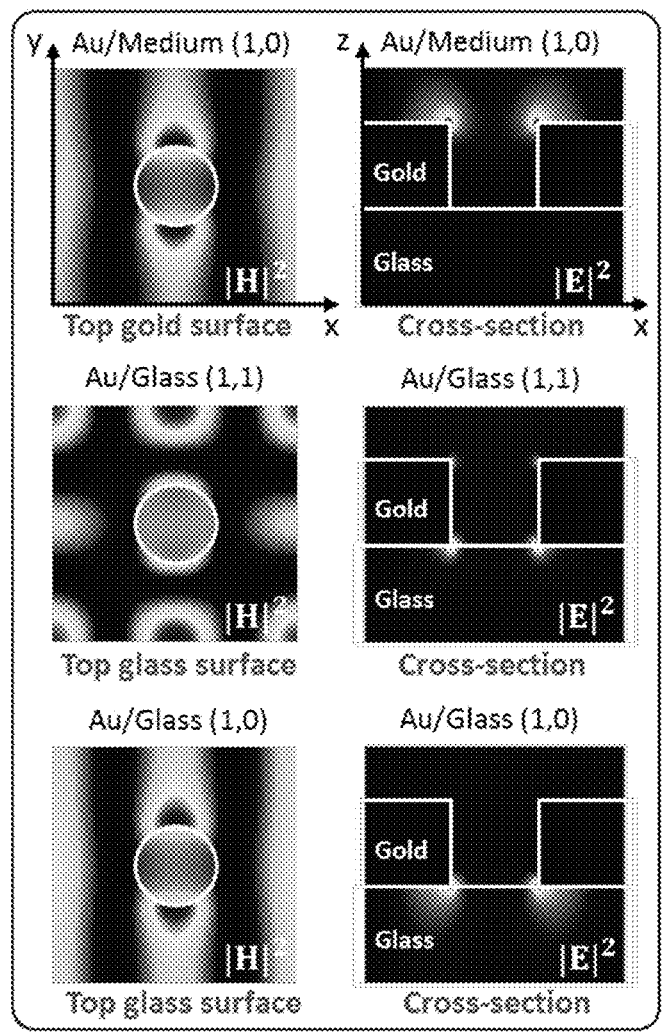
Figure 2D:
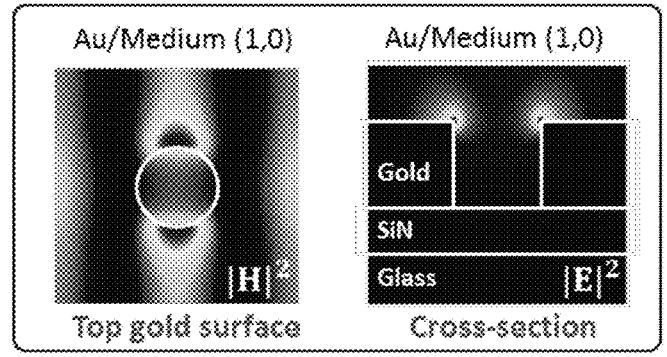

In order to understand how the multiple transmission resonances corresponding to Au/Glass modes are suppressed by a thin silicon nitride interlayer, the nearfield characteristics of the modes supported by the nanoholes for both substrates has been investigated in detail. As shown in FIG. 2A, for the nanohole system on glass, Au/Glass(1,1) mode indicated by the left arrow is spectrally located very close to the most sensitive Au/Medium(1,0) mode [Medium=Air], because glass, for example fused silica, has a low refractive index, $n_{glass}=1.42$. For the hybrid substrate, this mode is suppressed by the higher effective refractive index of the supporting layer (silicon nitride, $n_{SiN}=2.16$) with increasing silicon nitride thickness t, as shown in FIG. 2B leading to an elimination of multiple plasmonic nodes. FIGS. 2C and 2D show the corresponding magnetic ($|H|^2$) and electric ($|E|^2$) field intensity distributions calculated at the plasmonic resonances for both nanohole configurations. For the apertures on glass (t=0), we obtain the magnetic field intensity profiles at the air/metal interface (top surface of the metal film) for Au/Medium(1,0) mode [Medium=Air], and at the metal/glass interface at the bottom surface of the metal film for Au/Glass modes.

Electric field intensity profiles are calculated along the xz-cross section at y=0, where the electric field intensity is maximum. For example, see FIG. 7 for the region, where the cross-sectional electric field distributions are calculated. Magnetic field distributions that are shown in FIG. 2C at the left column corresponding to Au/Medium(1,0) mode [Medium=Air], and Au/Glass(1,0) modes show the expected symmetric standing field pattern along the x-direction which is due to two counter-propagating surface plasmons. On the other hand, for Au/Glass(1,1) mode, a diagonal standing wave pattern is observed due to the interference of multiple propagating surface plasmon excitations. For all the modes, hot spots along the y-direction are due to localized surface plasmon excitations. The magnetic field profiles clearly show that the transmission resonances uniquely incorporate both propagating and localized surface plasmons.

Figure 7:
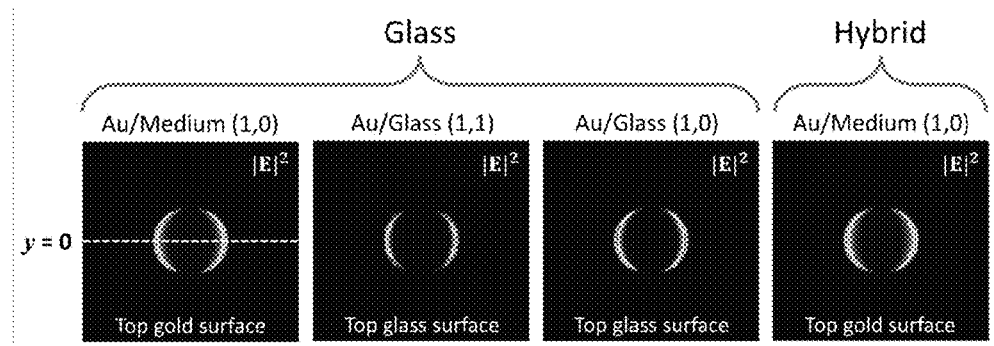
FIG. 7 shows representations of the analysis of nanohole arrays on glass and hybrid substrate.

Based on the electric field intensity distributions shown in the right column of FIG. 2C, plasmonic excitations for Au/Medium(1,0) mode [Medium=Air], are confined at the top surface of the gold film and extend deep into air. In contrast, for Au/Glass(1,0) and Au/Glass(1,1) modes, near-fields are mostly concentrated at the gold/glass interface. For example, FIG. 7 shows the dipolar characters of these modes through electric field intensity profiles calculated at the aperture plane.

FIG. 2B shows that as the silicon nitride thickness increases, Au/Glass(1,0) and Au/Glass(1,1) modes (denoted with a square and a circle, respectively) shift to longer wavelengths and their transmission intensities dramatically decrease. At thickness t=70 nm, they are suppressed within the wavelength region of interest. The aperture system supports a single well-defined transmission resonance due to the excitation of Au/Medium(1,0) mode [Medium=Air], as revealed by the magnetic field intensity distribution, see FIG. 2D, left column. The cross-sectional electric field profile of FIG. 2D, left column also demonstrates that the local electromagnetic fields are highly accessible as they are mainly concentrated at the top surface of the gold film and extends into the medium in their vicinity. Here, 70 nm silicon nitride interlayer is optically thin enough such that it does not compromise the transmission intensity.

On the other hand, a thick SiN layer is not desirable due to several reasons. Firstly, a thick SiN will compromise the signal strength of the EOT signal due to light absorption in the interlayer. Secondly, thick waveguide modes, such as >300 nm, could result excitation of waveguide modes and complicate the simple optical spectrum achieved with a thin SiN layer. For example, the publication to Tang et al., "Hybrid waveguide-surface plasmon polariton modes in a guided-mode resonance grating." Optics Comm., 2014, Vol. 285, pp. 4381-4386, this publication herewith incorporated by reference in its entirety, shows excitation of waveguide modes in a thick SiN layer, such as 327 nm, between a structured metallic film and a silicon oxide substrate. Also, 1D metallic stripes used in this work of Tang et al. are not suitable to excite EOT resonances due to its large slit width: 950 nm period with 50% duty cycle, i.e. 475 nm slit width. Thirdly, the biosensing performance of the Au/Medium (1,0) mode could be degraded due to spectral broadening and optical losses, for example linewidth broadening, thus FOM degradation, resulting from the coupling of the plasmonic mode with the waveguide modes that could be excited in a thick SiN interlayer. For these reasons, a preferably SiN interlayer thickness is for example between 70 nm-250 nm.

Figure 3A:
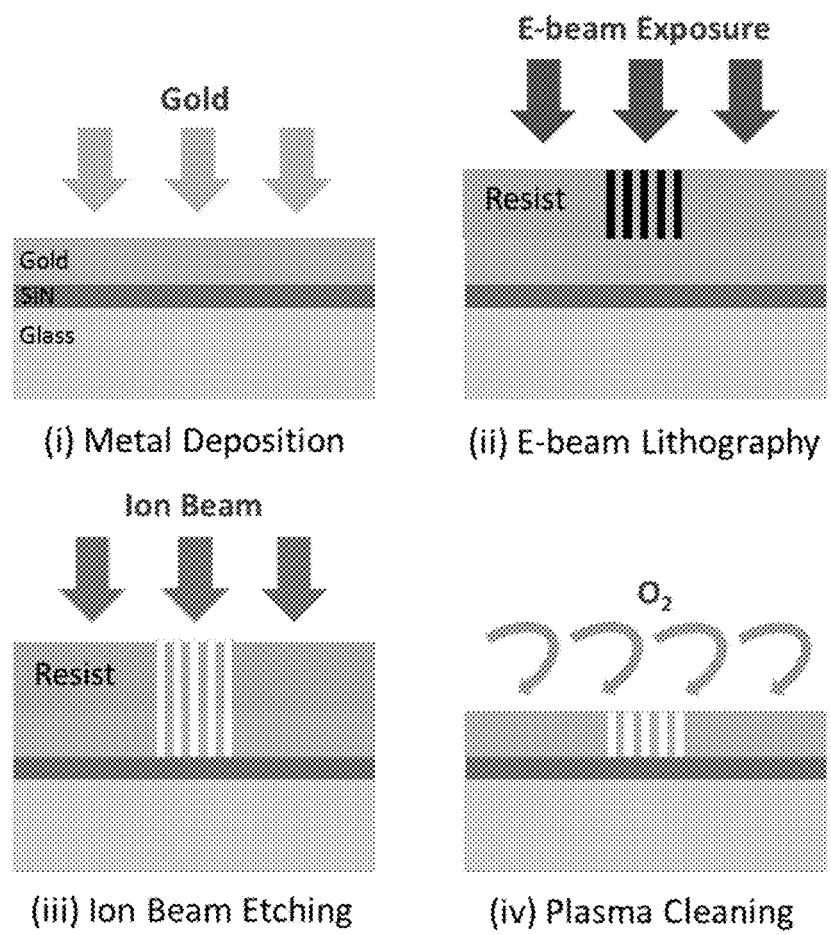
FIG. 3A depicts steps of the lift-off free nanofabrication scheme.
Figure 3B:
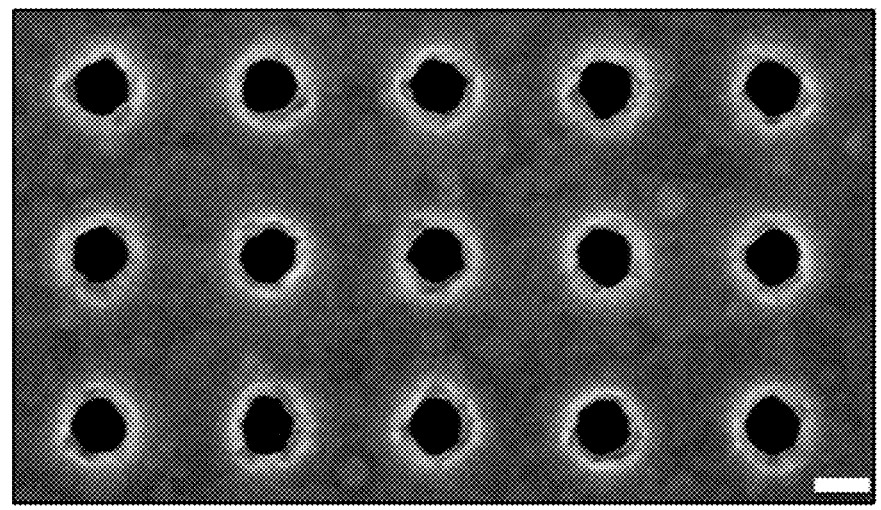
FIG. 3B shows SEM image of the fabricated nanoapertures on hybrid substrate having a scale bar of 200 nm.

In order to experimentally investigate the sensitivity of the nanohole arrays on hybrid substrate, an exemplary lift-off free fabrication scheme based on E-beam lithography has been tested, to fabricate the nanohole array on a hybrid substrate. FIG. 3A illustrates the exemplary fabrication steps. We first deposit 5 nm chromium and 120 nm gold (done with a Leybold™ Optics LAB-600H E-beam evaporator) on a 500 μm thick fused silica coated with 90 nm low pressure chemical vapor deposited silicon nitride film. In a next step, an E-beam lithography (Vistec™ EBPG5000) on a positive resist (495-A4 PMMA) is performed to define nanohole arrays. After development, in a next step, the metal film is etched by ion beam milling (Veeco™ Nexus IBE350) by using the resist as a mask. Finally, a plasma cleaning step (TEPLA 300 plasma stripper) is performed to remove the remaining resist on the gold surface. FIG. 3B shows the scanning electron microscopy (SEM) image of the fabricated nanoholes with 200 nm hole diameter and 600 nm array periodicity.

Figure 3C:
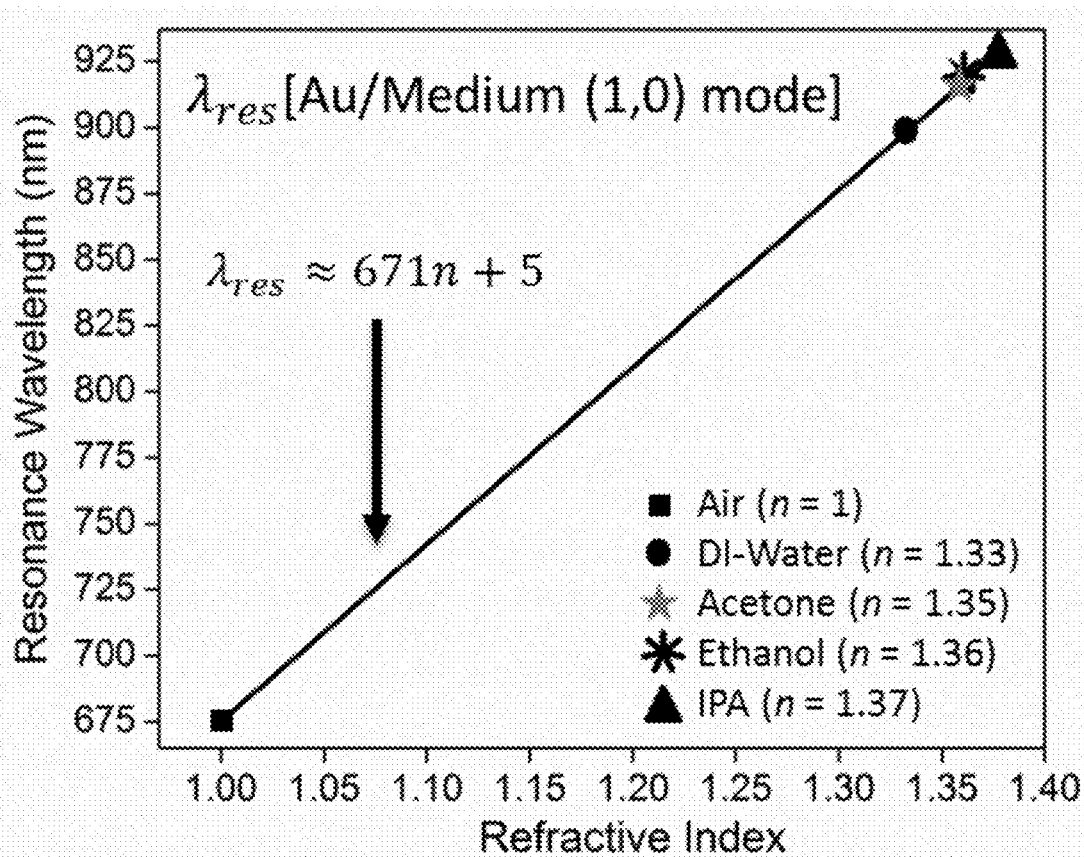
FIG. 3C shows a resonance wavelength of Au/Medium(1,0) mode vs. refractive indices of bulk solutions, $n_{DI-Water} \approx 1.33$, $n_{Acetone} \approx 1.35$, $n_{Ethanol} \approx 1.36$, and $n_{IPA} \approx 1.37$. The preferred device parameters used in the experiments are hole diameter is 200 nm, array periodicity is 600 nm, thicknesses of the gold film and silicon nitride interlayer are 120 nm and 90 nm, respectively.

The sensitivity of the aperture system of the nanohole array is measured by monitoring the spectral variations within Au/Medium(1,0) mode after introducing bulk solutions with different refractive indices, including deionized water $n_{DI-Water} \approx 1.33$, acetone $n_{Acetone} \approx 1.35$, ethanol, $n_{Ethanol} \approx 1.36$, and IPA (isopropanol) $n_{IPA} \approx 1.37$ as shown in FIG. 3C. Moreover, FIG. 8 shows the details of the experimental setup utilized for the optical characterization of the nanohole arrays, including a halogen lamp, a light condenser lens, the plasmonic chip with the nanohole array, an objective lens, a mirror, fiber coupling optics and fiber, and a spectrometer. In the optical characterization, integration time is 200 ms with 10 averaged spectrum frames. The sensor measurements are performed over a 100 μm×100 μm area. With the measured resonance wavelength of Au/Medium(1,0) mode for each bulk solution, a linear relationship is determined as follows: $\lambda_{res} \approx 671\ n+5$. This result shows that nanohole arrays on hybrid substrate exhibit a refractive index sensitivity (S=Δλ/Δn) as large as 671 nm/RIU. Supporting spectrally sharp transmission resonances as narrow as ~16 nm, the aperture system shows a figure-of-merit value as large as FOM=~42. Note that this FOM value is calculated for bulk solutions and it is more complex for biosensing applications, which depends on the size of the biomolecules and capturing mechanism. These refractive index sensitivity and figure-of-merit values are highly advantageous for label-free biosensing applications demanding high sensitivities to change in surface conditions.

The nanohole array according to one aspect of the present invention allows to perform label-free sensing. In order to demonstrate the advantageous of the nanohole system on hybrid substrate over glass, we carry out label-free detection of protein bilayers by monitoring spectral variations within the plasmonic modes due to biomolecular bindings. In the experiments, we use a protein bilayer composed of protein A/G (from Pierce) and protein IgG (goat IgG from Sigma), which selectively binds on gold. This can be seen in the passages related to FIGS. 7-10 shown below, for protein chemistry and sample preparation techniques.

Figure 4A:
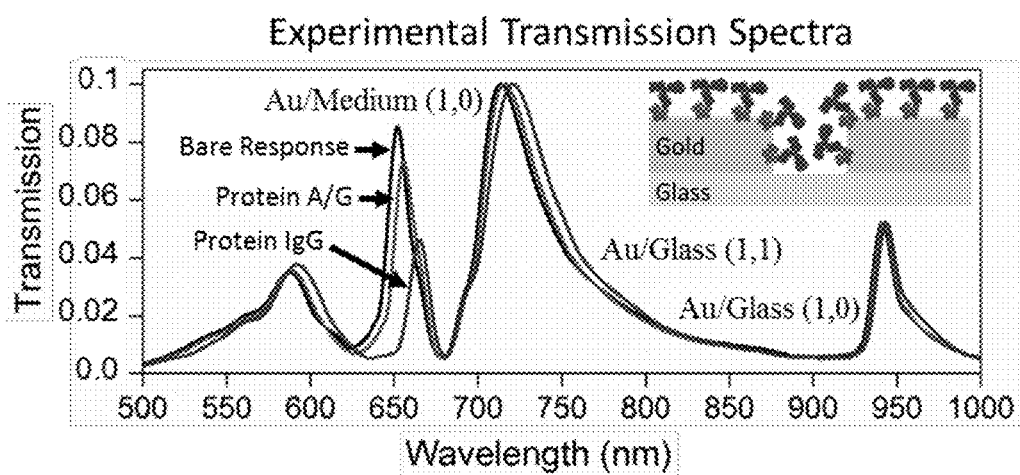
FIG. 4A depicts experimental transmission spectra of the nanohole arrays on glass.
Figure 4B:
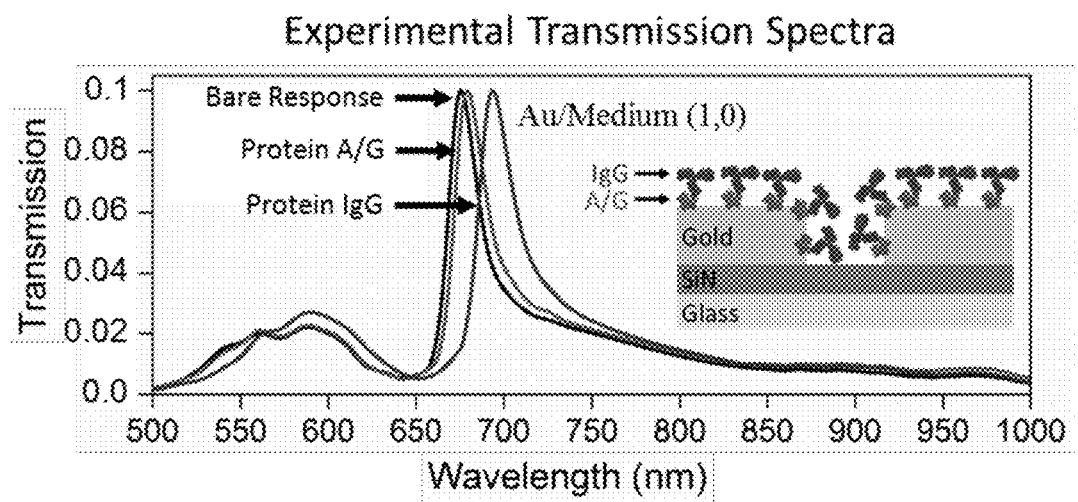
FIG. 4B depicts experimental transmission spectra on a hybrid substrate, where the gold surface is covered with a bilayer consisting of proteins A/G and IgG.
Figure 4C:
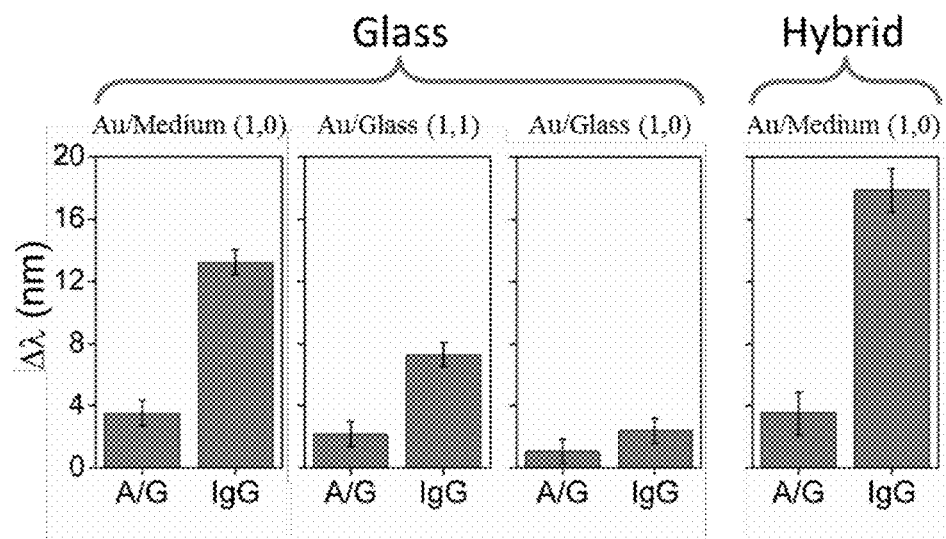
FIG. 4C shows the spectral shift amounts for the plasmonic modes supported by the nanohole systems on glass and hybrid substrate.

FIGS. 4A and 4B show the spectral variations within the plasmonic modes supported by the nanohole arrays on glass and hybrid substrate, respectively. In these figures, transmission responses after the addition of protein A/G and protein IgG, respectively are shown. FIG. 4C shows the spectral shift amounts within each plasmonic mode (mean values with error bars calculated by adding twice the standard deviation from 3 independent experiments). Here, Au/Medium(1,0) mode [Medium=Air] of the hybrid substrate exhibits larger spectral shifts compared to the same mode supported by glass. Upon functionalization of nanoholes with protein mono- and bilayer, containing 0.5 mg/mL protein A/G and 0.5 mg/mL protein IgG, for hybrid substrate, Au/Medium(1,0) mode [Medium=Air] shifts to longer wavelengths by ~4 nm and ~18 nm, whereas it shifts by ~3 nm and ~13 nm for glass. More importantly for the nanohole system on glass, spectrum of Au/Medium(1,0) mode [Medium=Air] starts to overlap with Au/Glass(1,1) mode. Furthermore, its transmission intensity decreases as it shifts to longer wavelengths. A larger sensitivity by Au/Medium(1,0) mode [Medium=Air] is due to its highly accessible large local electromagnetic fields resulting in a better spatial overlap between optical fields and biomolecules. In contrast, nearfields for Au/Glass modes are mostly inaccessible as they are concentrated along the gold/glass interface. Consequently, with the coverage of protein A/G and protein IgG, Au/Glass(1,1) [Au/Glass(1,0)] mode shifts only ~2 nm [~1 nm] and ~7 nm [~2 nm], respectively.

Figure 5A:
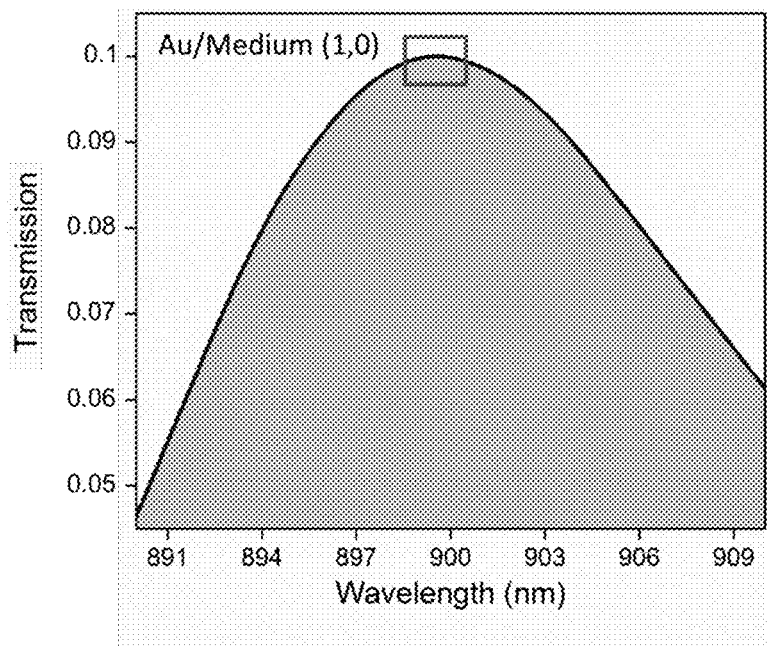
FIG. 5A shows experimental transmission spectra of the nanohole arrays on hybrid substrate embedded in 0.1% and 0.25% ethanol concentrations shown for Au/Medium(1,0) with ethanol being the medium within an 8 nm wavelength range at the resonance peak.
Figure 5B:
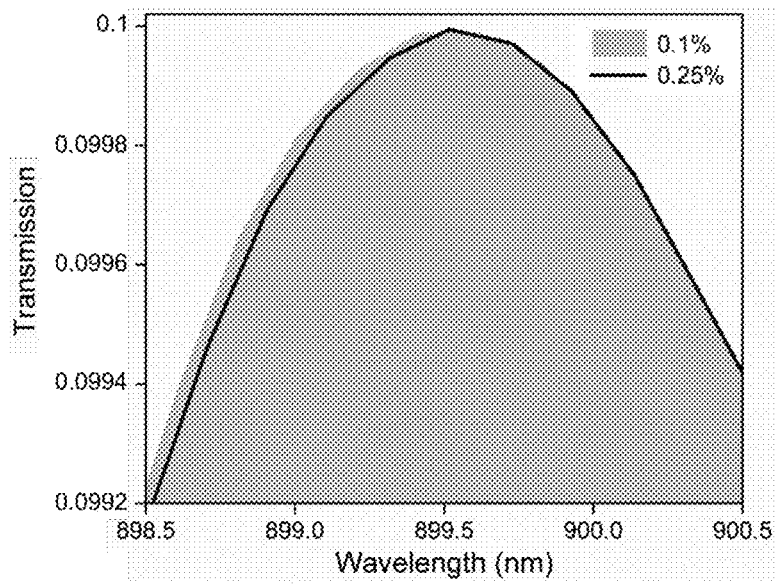
FIG. 5B shows transmission spectra zoomed in within a 2 nm wavelength range denoted with a square in FIG. 5A to highlight the collective spectral shifts along the left-hand side of Au/Medium(1,0) mode with ethanol as the medium.

According to another aspect of the present invention, a spectral integration method for low limit-of-detection is provided. For label-free optical biosensors, one of the most common operation methods is to monitor the changes in the resonance wavelength. However, this method is limited for determining minor refractive index changes as it relies on spectral information only at a single wavelength. In contrast, it has been shown that using spectral data in a broad wavelength range near the resonance can significantly improve the sensitivity. For example, FIGS. 5A and 5B show the experimental response of the nanohole system on hybrid substrate embedded in 0.1% (red region) and 0.25% (black curve) ethanol solutions for Au/Medium(1,0) mode [Medium=Ethanol] near its resonance within 8 nm and 2 nm wavelength ranges, respectively. For both cases, we do not observe a significant wavelength shift in the resonance wavelength with the resulting refractive index change of only $2 \times 10^{-5}$ RIU. On the other hand as shown in FIG. 5B, a collective red-shift along the left shoulder of the Au/Medium(1,0) [Medium=Ethanol] resonance is clearly observable. In order to utilize this shift, we integrate the transmission intensity of Au/Medium(1,0) mode [Medium=Ethanol] within a spectral window for different refractive indices. In order to reliably differentiate the integral values corresponding to different refractive indices, we investigate width and central wavelength of the spectral window used in the integration. Due the asymmetric line-shape of Au/Medium (1,0) mode [Medium=Ethanol], we observe that the spectral window covering the wavelengths between the resonance wavelength of Au/Medium(1,0) mode [Medium=Ethanol] and the transmission minimum on the left-hand side due to Wood's anomaly gives the most reliable integral variations. The spectral windows for both nanohole configurations are illustrated in FIG. 9.

Figures 5C, 5D:
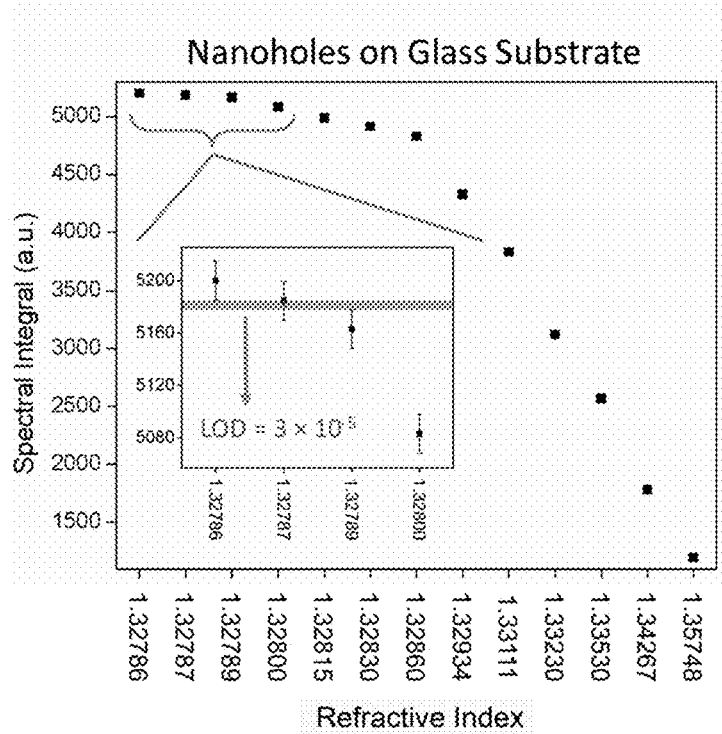
FIG. 5C shows spectral integral values calculated for the nanohole systems, embedded in different refractive indices of ethanol solutions on a glass substrate.
FIG. 5D shows the same for a hybrid substrate.

FIGS. 5C and 5D are the spectral integral values for the aperture systems on glass and hybrid substrate embedded in different refractive indices of bulk ethanol concentrations in DI-water ranging from 0.1% to 100%. As the refractive index of the medium increases with ethanol concentration, the spectrum red-shifts and the integral value gradually decreases. The two figure insets show the zoom of the integral values corresponding to the lowest ethanol concentration. Here, the limit-of-detection (LOD) of the aperture system is defined as the minimum distinguishable refractive index change between the two distinguishable spectral integral values. LOD (indicated by green) has been calculated by adding twice the standard deviation to the mean integral value for the corresponding concentrations obtained from 3 independent experiments. For the system on glass, a minimum detectable refractive index change of $3 \times 10^{-5}$ RIU is obtained. Integral values corresponding to 0.25% ethanol solution and DI-water, where n=1.32789 and 1.32786, can be reliably differentiated. In contrast, the aperture system on hybrid substrate according to another aspect the present invention supports 1.5 fold higher refractive index sensitivities with a detection limit as low as $2 \times 10^{-5}$ RIU. Integral values corresponding to 0.25% and 0.1% ethanol solutions, where n=1.32789 and 1.32787, can be reliably differentiated. Recently, different methods to improve the refractive index sensitivity have been demonstrated utilizing plasmonics platforms combined with post-processing methods, showing down to $10^{-6}$ RIU sensitivity levels. In particular, spectral integration method utilized here yields similar sensitivity values with the previously introduced centroid method.

Figure 6A:
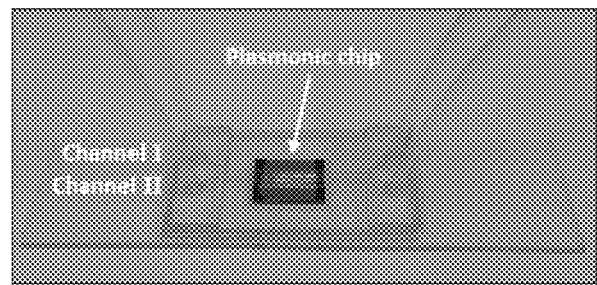
FIG. 6A shows a photograph and FIG. 6B a schematic illustration of the plasmonic biosensor integrated with dual-channel microfluidics. Exponential behaviour of the association phase of is shown in FIG. 6C at 1000 ng/mL and in FIG. 6E at 0.7 ng/mL IgG on A/G determined by the spectral integral method.
Figure 6B:
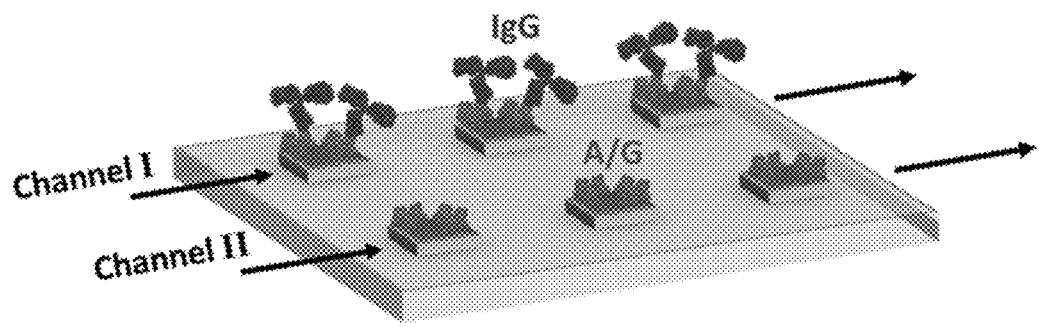
FIG. 6D shows spectral integral value calculated for different IgG concentration, and shows an inset with the limit-of-detection (LOD) of the aperture system. Note that the initial integral values of the exponential curves are the same (I(t=0)=5116) for each IgG concentration such that we can reliably use the integral values at minute 50 for determining kinetics constants.
Figure 6C:
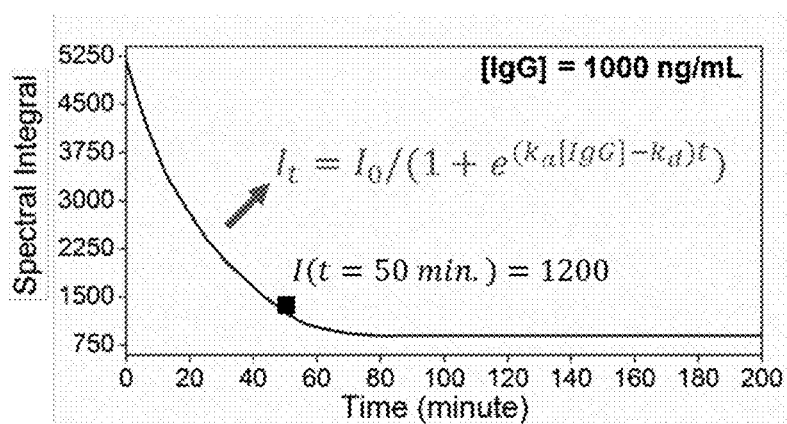

Using the spectral integration method, successful demonstration of label-free and real-time analysis of protein binding kinetics has been shown. FIGS. 6A and 6B show the photograph and the schematic illustration of the plasmonic biosensor integrated with dual-channel microfluidics used in the experiments. Moreover, FIG. 10 shows the structure of the microfluidic chamber design. Initially, the sensors are functionalized with 0.5 mg/mL protein A/G. In Channel I, we inject protein IgG (in a PBS solution). Channel II is used as a control, where we inject PBS (phosphate buffered saline) with the same flow rate to determine the integral variations due to optical, mechanical and chemical fluctuations. FIG. 6C shows the time dependence of the integral value due to the binding of 1000 ng/mL protein IgG on protein A/G, reaching to saturation after ~80 minutes. Next, the real-time behaviour is fitted to an exponential equation to determine the association phase of protein IgG on protein A/G.

$$I_t = I_0/(1+e^{(k_a[IgG]-k_d)t}) \qquad (2)$$

Figure 6D:
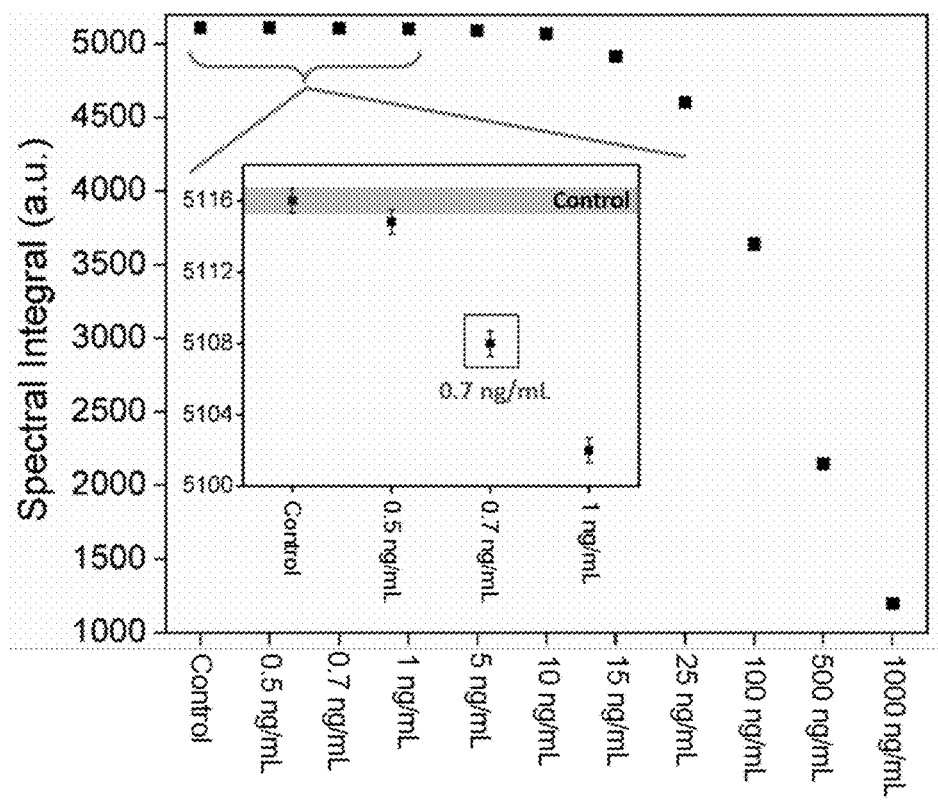
Figure 6E:
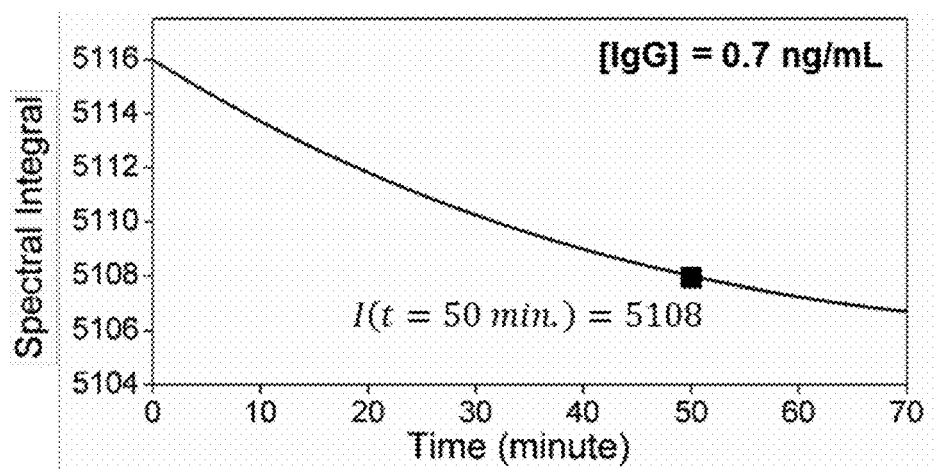

Here, $k_a$ and $k_d$ are the association and disassociation constants, respectively. Dissociation constant for mouse IgG on protein A/G is $k_d < 1 \times 10^{-6}$ s$^{-1}$, indicating that the composite is highly stable once it is formed, and a minimum amount of IgG will remain unbound. Using the exponential fitting and $k_d$ value for [IgG]=1000 ng/mL, the association constant is calculated as $k_a = 2.37 \times 10^5$ M$^{-1}$s$^{-1}$. These results, comparable to conventional SPR, confirm that binding kinetics of proteins can be reliably extracted. We next perform analysis at different IgG concentrations and determine the spectral integral values from the exponential curves at 50 minute. FIG. 6D shows the integral values for different IgG concentrations in the range between 0.5 ng/mL to 1000 ng/mL. As shown in the zoom image in FIG. 6D, the integral value of control determines the detection limit of our biosensing platform, indicated by the grey area, and calculated by adding twice the standard deviation to the mean integral value for the corresponding IgG concentrations. The results show that IgG concentrations can be reliably detected down to 0.7 ng/mL. This low limit-of-detection value is highly promising for label-free and real-time analysis of biomolecular binding kinetics at low analyte concentrations. Importantly as shown in FIG. 6E, employing spectral integration method, biomolecular binding kinetics even at 0.7 ng/mL level can be measured. For this IgG concentration, a similar association constant is calculated, $k_a = 2.29 \times 10^5$ M$^{-1}$s$^{-1}$.

FIG. 7 shows a results of a nearfield analysis of nanohole arrays on glass and hybrid substrate. Electric field intensity ($|E|^2$) distribution is calculated at the top gold (glass) surface for Au/Air (Au/Glass) modes. The figure demonstrates the dipolar character of the modes, where the local electromagnetic fields are concentrated at the rims of the apertures along the polarization direction (x). The cross-sectional electric field profiles in FIGS. 2C and 2D are calculated at y=0, denoted with a red dashed line.

FIG. 8 shows a system that can be used as an experimental setup for the optical characterization of the nanohole arrays. Optical characterization of the nanohole arrays is performed through spectroscopy measurements, where an unpolarized broadband white light source was used. Light transmitted from the plasmonic chip is collected by a high-magnification objective lens, for example a 100× Nikon™ objective lens with NA: 0.6 embedded in a Nikon™ Eclipse-Ti microscope, coupled into an optical fiber and then recorded with a SpectraPro™ 500i spectrometer. Transmission spectra are determined by taking the ratio between the spectra of light transmitted from the aperture system and the spectra of the bare light source. This method can be used to consider the spectral shape of the halogen light source in order to accurately determine the linewidth of the plasmonic resonances.

Figure 9A:
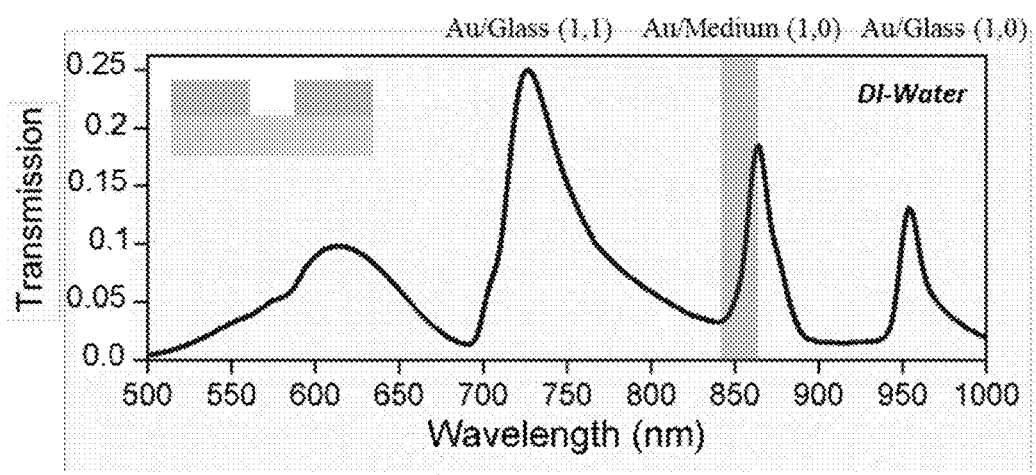
FIGS. 9A and 9B show graphs representing experimental transmission spectra of the nanohole arrays on glass and hybrid substrate embedded in DI-water.
Figure 9B:
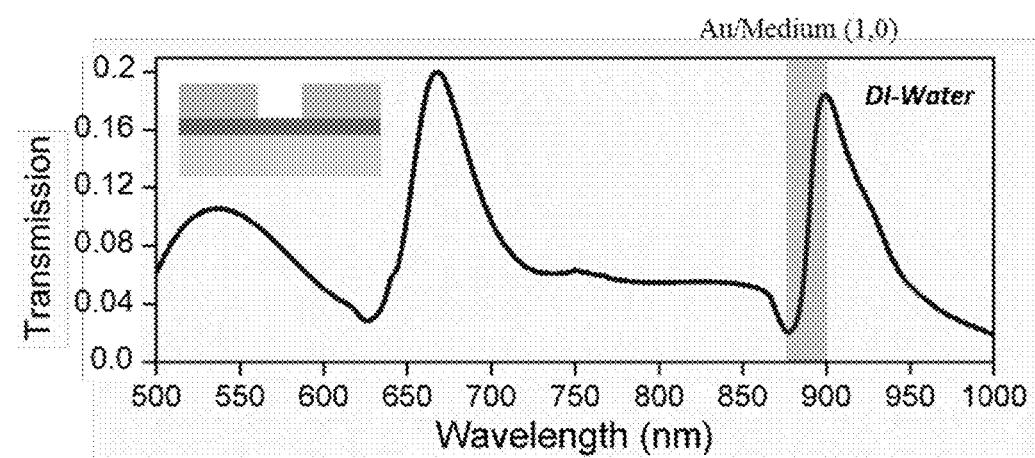

FIGS. 9A and 9B shows two graphs showing experimental transmission spectra of the nanohole arrays on glass and hybrid substrate embedded in DI-water. In FIG. 9A, for the aperture system on glass, since Au/Glass(1,0) and Au/Glass (1,1) modes support low sensitivities, only ~12 nm (from ~714 nm to ~726 nm) and ~13 nm (from ~941 nm to ~954 nm) shifts, respectively, are observed. In contrast, Au/Air (1,0) mode shifts from ~652 nm to ~864 nm and now spectrally locates between two Au/Glass modes such that for the ethanol concentration tests, we no longer observe a spectral overlap, as it exists for the dry measurements shown in FIG. 1b and FIG. 4a in the main text. (b) For the aperture system on hybrid substrate, Au/Air(1,0) mode shifts from ~675 nm to ~899 nm. For both figures, green areas denote the region where we perform the spectral integration.

FIG. 10 shows a schematic representation of dual-channel microfluidic chamber design. Multiple optically transparent polyolefin sheet with 50 μm thickness, one side is coated with adhesive glue, are assembled for creating layers, all 5 layers are represented in FIG. 10 for the design of the microfluidic chamber. Top layer contains inlet and outlet tube connections with a square opening allowing optical transparency. Second layer provides a robust stand for the tubings. Third layer possesses the dual microfluidic channels. Fourth layer contains two square frames, stabilizing the plasmonic chip and minimizing the sensing volume around the sensors. Bottom layer contains the plasmonic chip.

In conclusion, a biosensing platform employing plasmonic nanohole arrays on a hybrid substrate is presented, and a method of manufacturing the same. The system supports spectrally well-isolated and sharp optical responses, which are highly sensitive to surface conditions. Utilizing a high refractive index dielectric interlayer between gold film and glass, the nanoaperture system suppresses the additional plasmonic modes arising from the low refractive index of the transparent material utilized in the conventional nanohole designs. In the absence of spectral overlaps and amplitude variations, the strong optical response of the nanohole arrays on hybrid substrate is easy-to-track for reliable monitoring of spectral variations. Furthermore, we improve the detection limit of our biosensing platform by integrating the spectral information in a large wavelength range instead of monitoring the changes only within the resonance wavelength and demonstrate a limit-of-detection as low as $2\times10^{-5}$ RIU. We also successfully perform real-time detection of biomolecular binding kinetics in sub-1 ng/mL concentration, which is highly advantageous for label-free biosensing at ultra-low analyte concentrations.

While the invention has been disclosed with reference to certain preferred embodiments, numerous modifications, alterations, and changes to the described embodiments, and equivalents thereof, are possible without departing from the sphere and scope of the invention. Accordingly, it is intended that the invention not be limited to the described embodiments, and be given the broadest reasonable interpretation in accordance with the language of the appended claims.

The invention claimed is:

1. A biosensor system comprising:
   a microfluidic channel; and
   a biosensor device located in the microfluidic channel, wherein the biosensor device includes,
     a metal layer;
     a transparent substrate layer; and
     a dielectric layer;
     wherein the metal layer includes a plurality of sub-wavelength apertures,
     wherein the dielectric layer is located between the metal layer and the transparent substrate layer to form a spectrally isolated and well-defined optical transmission resonance through the extraordinary optical transmission (EOT) phenomenon, and
     wherein the biosensor device is configured for optical label-free biodetection of at least one substance in a sample based on refractive index sensing when the sample is introduced into the microfluidic channel so as to contact the biosensor device.

2. The biosensor system according to claim 1, wherein the dielectric layer has a refractive index value higher than the substrate layer.

3. The biosensor system according to claim 1, wherein the dielectric layer has a thickness between 70 nm and 250 nm.

4. The biosensor system according to claim 1, wherein a diameter of each one of the sub-wavelength apertures is between 100 nm and 220 nm.

5. The biosensor system according to claim 1, wherein a refractive index of the dielectric layer is more than 2.

6. The biosensor system according to claim 1, wherein the dielectric layer of the biosensor device includes silicon nitride.

7. The biosensor system according to claim 1, further comprising:
   a spectrometer configured to measure an optical transmission spectrum of a substance to be identified in the microfluidic channel and to integrate spectral information of the optical transmission spectrum in a predetermined wavelength range to improve a detection limit.

8. A method for carrying out bio-sensing, the method comprising the steps of:
   providing a biosensor device in a microfluidic channel, the biosensor device including a metal layer, a transparent substrate layer, and a dielectric layer, the metal layer having a plurality of sub-wavelength apertures, and the dielectric layer located between the metal layer and the transparent substrate layer to form a spectrally isolated and well-defined optical transmission resonance through the extraordinary optical transmission (EOT) phenomenon;
   introducing a sample containing at least one substance to be identified into the microfluidic channel so that the at least one substance contacts the plurality of sub-wavelength apertures of the metal layer;

measuring an optical transmission spectrum of the least one substance to be identified; and performing optical label-free biodetection of the at least one substance based on refractive index sensing.

9. The method according to claim 8, further comprising the step of:

monitoring changes of a resonance wavelength of the optical transmission spectrum.

10. The method according to claim 8, further comprising the step of:

integrating spectral information of the optical transmission spectrum in a predetermined wavelength range to improve a detection limit.

11. The method according to claim 8, wherein the dielectric layer has a refractive index value higher than the substrate layer.

12. The method according to claim 8, wherein the dielectric layer has a thickness between 70 nm and 250 nm.

13. The method according to claim 8, wherein a diameter of each one of the sub-wavelength apertures is between 100 nm and 220 nm.

14. The method according to claim 8, wherein a refractive index of the dielectric layer is more than 2.

15. The method according to claim 8, wherein the dielectric layer of the biosensor device includes silicon nitride.

* * * * *